United States Patent
Kok et al.

(10) Patent No.: US 7,588,790 B2
(45) Date of Patent: Sep. 15, 2009

(54) PROCESS FOR THE REMOVAL OF UNDESIRED FLAVOUR AND ODOUR COMPONENTS FROM POTASSIUM LACTATE

(75) Inventors: Symone Kok, Giessenburg (NL); Robert Patrick Lobbes, Leusden (NL); Arielle Regine De Jong, De Bilt (NL); Bert Theo De Vegt, Rotterdam (NL)

(73) Assignee: Purac Biochem B.V., Gorinchem (NL)

( * ) Notice: Subject to any disclaimer, the term of this patent is extended or adjusted under 35 U.S.C. 154(b) by 439 days.

(21) Appl. No.: 10/477,134

(22) PCT Filed: May 7, 2002

(86) PCT No.: PCT/NL02/00300

§ 371 (c)(1),
(2), (4) Date: Apr. 28, 2004

(87) PCT Pub. No.: WO02/090311

PCT Pub. Date: Nov. 14, 2002

(65) Prior Publication Data

US 2004/0171878 A1 Sep. 2, 2004

(51) Int. Cl.
*A23L 1/00* (2006.01)
*A23P 1/00* (2006.01)
(52) U.S. Cl. .................. 426/486; 426/478; 426/487; 426/488; 426/534
(58) Field of Classification Search .................. 426/478, 426/486, 487, 488, 534, 650
See application file for complete search history.

(56) References Cited

U.S. PATENT DOCUMENTS 2,071,368 A 2/1937 Weisberg et al.
7,494,684 B2 * 2/2009 Cruz et al. .................. 426/652

FOREIGN PATENT DOCUMENTS

GB 934695 8/1963

OTHER PUBLICATIONS

Roy, G.M., An 370462 Frosti, abstracting Activated carbon applications in ghe food and pharmaceutical industries., Published by: Technomic Publishing Company., Lancaster, PA 1995 65-80.*
Marcel Wilmink, "Solving a Meat Problem," International Food Ingredients, 2000, pp. 52-53, No. 6, XP-002213993.
Frank Systermans, "Lactates—A New Trend in Fresh Marinated Meat," 2000, 2 pages, XP-002213994.
"Purasal® P HiPure 60 specification," Purac Internet Site <www.purac.com.products>, Rev. No. 1/3102, 1 page.
International Search Report for PCT/NL02/00300, Date of Completion: Sep. 19, 2002, Date of Mailing: Oct. 11, 2002.

* cited by examiner

*Primary Examiner*—Leslie Wong
(74) *Attorney, Agent, or Firm*—Gilberto M. Villacorta; Sunit Talapatra; Foley & Lardner LLP

(57) ABSTRACT

The present invention relates to a process for the removal of undesirable flavours and odours from potassium lactate, wherein the potassium lactate is treated with active carbon. According to this method a potassium lactate is obtained which does not have the bitter aftertaste of the potassium lactate according to the state of the art.

9 Claims, 1 Drawing Sheet

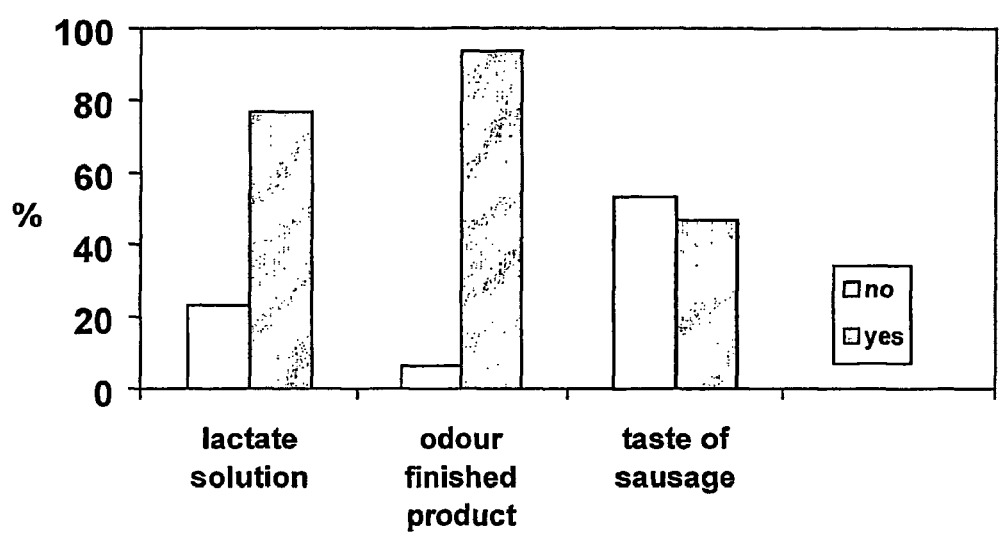

PROCESS FOR THE REMOVAL OF UNDESIRED FLAVOUR AND ODOUR COMPONENTS FROM POTASSIUM LACTATE

CROSS REFERENCE TO RELATED APPLICATIONS

This Application is a National Phase Filing Under 35 U.S.C. § 371 based on International Application No. PCT/NL02/00300 filed May 7, 2002 (published Nov. 14, 2002 under International Publication Number WO 02/090311 A1) and claims priority to U.S. application Ser. No. 09/851,081 filed May 9, 2001, now abandoned both of which are hereby incorporated by reference in their entireties.

The present invention relates to a process for the removal of undesirable flavours and odours from potassium lactate. The invention further relates to the potassium lactate obtained with such a process and the use thereof in foodstuffs such as meat and sauces.

Potassium lactate is a product, which is mainly used in the meat industry. It is used in the same application as sodium lactate, namely for shelf life extension and safety enhancement. The use of potassium lactate is more and more preferred since it is believed that the use of sodium can cause hypertension. The disadvantage of most potassium salts, however, is their flavour. They cause a bitter aftertaste. There is therefore a need for a potassium lactate having improved flavour and odour properties.

It has now been found that the undesired flavour and odour substances can be removed from potassium lactate by treating it with active carbon. The resulting potassium lactate is less bitter and has a very favourable flavour and odour profile and is thus accepted by a large part of the population.

BRIEF DESCRIPTION OF THE DRAWING

FIG. 1 shows the percentage of panelists that are able to taste a difference between commercially available untreated potassium lactate and potassium lactate treated according to the invention.

According to the present invention the active carbon used is preferably pre-treated by washing with hydrochloric acid and neutralising with sodium bicarbonate. The active carbon preferably has a particle size of 0.5 to 3 mm, more preferably 0.9 to 1.1 mm. The active carbon is based on mineral coal.

The potassium lactate is treated in the form of an aqueous solution. The concentration of potassium lactate in the solution to be treated is 40 to 80% by weight, based on the combined weight of water and potassium lactate. The amount of active carbon is about 0.5 to 2 grams active carbon per kg potassium lactate. The temperature of the solution is generally 20-60° C.

As indicated-above, potassium lactate is used as an additive in the meat industry. Other foodstuff additives normally used in the meat industry such as acetic acid, sodium acetate, sodium diacetate, potassium acetate, potassium diacetate, citric acid, sodium citrate and potassium citrate may also be present in the potassium lactate solution. It was found that active carbon treatment does not detrimentally affect the taste and odour of the other foodstuff additives.

The process according to the present invention can be carried out continuously or batch wise. In a batch wise process the active carbon is mixed with the solution of potassium lactate and stirred. After a contact time of 20 to 40 minutes the active carbon and the potassium lactate solution are separated, preferably by filtration.

However, it is preferred to carry out the present invention continuously. In that case the active carbon is present in a column through which the potassium lactate solution is passed in a downward or upward direction. Preferably the potassium lactate solution is supplied to the top of the column and moved downward through the column. To this end, suitable pumping means can be connected to the column.

After leaving the column the potassium lactate solution is subjected to filtration to remove any remaining active carbon. Preferably the filtration is carried out in two steps, the first step consisting of removal of particles larger than 1 µm, the second step of removal of particles larger than 0.5 µm.

The residence time of the potassium lactate solution in the column of active carbon will generally be from 20 to 40 minutes. According to the present invention also a combination of several columns of active carbon, for instance two columns in parallel, can be used.

The present invention also provides an apparatus for carrying out the process, which comprises a column filled with active carbon, connected to pumping means for supplying the potassium lactate solution to be treated and suitable piping to connect the pumping means to the active carbon column. The output of the active carbon column is connected through suitable piping to one or more filters. Examples of suitable filters are bag filters.

The present invention also relates to the potassium lactate or potassium lactate-containing liquid or solution obtained with the process described above. This potassium lactate, potassium lactate-containing liquid or solution is characterised by a flavour profile in which the following characteristics are substantially absent: metal flavour and bitterness. It is further characterised by an odour profile in which the following characteristics are substantially absent: intense odour, pungent odour, harsh odour and ferrnentative odour.

The potassium lactate, the potassium lactate-containing liquid or solution obtained can be used in foodstuffs. It will be present in the foodstuffs up to a level of 5-weight % based on the total weight of the foodstuff. Examples of foodstuffs are meat and poultry products, ready to eat meals, soups and sauces. The potassium lactate provides for a high safety level of the meat and poultry products and a longer shelf life of food products in general, without negatively effecting the sensory properties of the end product. The foodstuffs indicated have a pH of 5 to 8.

The potassium lactate, potassium lactate-containing liquid or solution may be added at any time during preparation of the foodstuff. It may even be added to the foodstuff after preparation.

As mentioned-above, the treated potassium lactate can be used in combination with other food acids and their derivatives, such as acetic acid, sodium acetate, sodium diacetate, potassium acetate, potassium diacetate, citric acid, sodium citrate and potassium citrate. Said additional foodstuff additives may be added separately to the foodstuff or in combination with the treated potassium lactate, potassium lactate-containing liquid or solution.

EXAMPLES

In the examples a column of active carbon obtained from Chemviron carbon is used containing Food Grade Cyclesorb HP. This column has the following characteristics:

| | |
|---|---|
| volume carbon: | 2 m³ |
| volume vessel: | 2.35 m³ |
| diameter: | 1500 mm |
| height: | 2300 mm |

Two of these vessels in parallel were used. The flow rate of potassium lactate through the columns is 5 m³/hour. The temperature is 35° C. The columns are combined with two filters. The first filter is a bag filter eliminating all particles larger than 1 μm. The second filter is a filter removing particles larger than 0.5 μm.

Example 1

A tasting test was carried out with sausages containing both treated and untreated potassium lactate. For the taste test solutions of 1.25% lactate in water were prepared. These batches were used also for odour tests. For the taste test in cooked sausages 3% of potassium lactate (either treated or untreated) was added to the meat dough. For this test a standard recipe of cooked sausages was used. Table 1 gives the composition of the meat dough. All tests were done in a triangle test.

TABLE 1

Composition of the meat dough

| Ingredients | Dosage (%) |
|---|---|
| Minced beef | 10 |
| Minced pork | 42.5 |
| Minced pork fat | 35 |
| Water/ice | 10 |
| Spice-mix | 0.35 |
| Sodium ascorbate | 0.05 |
| Cutter phosphate | 0.3 |
| Colorozo | 1.8 |
| (salt + nitrite) | |

The sausages were prepared by placing the minced beef, pork and pork fat in a chopping bowl. These three ingredients were chopped for approximately 1 minute. The ice and the rest of the ingredients were added. The entire mixture was chopped for approximately 5 minutes. The total batch was divided into smaller batches. The desired additive was added to the batch and chopped for 3 minutes. The mixture obtained was filled into artificial casings with a diameter of 35 mm. The sausages obtained were cooked for 45 minutes at 80° C. (the internal temp. of the sausages will be 72° C.). Next the sausages were cooled till room temperature and quickly frozen at −34° C.

Results

In the tasting test of the purified potassium lactate solution in water there is a significant difference between the potassium lactate before and after purification. The purified potassium lactate tastes less bitter. Their odour of the treated potassium lactate in water is also significantly less than that of the non-treated potassium lactate. In sausages 47% of the panellists finds a difference in taste.

The results are shown in FIG. 1, which shows the percentage panellist that are able to taste difference between commercially available untreated potassium lactate and potassium lactate treated according to the invention.

Example 2

A tasting test was carried out with chicken sausages containing sodium lactate, treated and untreated potassium lactate. All samples contained 2.5 and 3.3% lactate respectively.

The sausages were prepared by cutting the chicken meat in small pieces, adding 0.5% phosphate and 1.5% salt and mixing well. The meat was stored in the refrigerator for 18 hours. The total batch was divided into smaller batches. The desired additive was added to the batch. The mixture obtained was filled into casings and pasteurised for 45 minutes at 80° C. The sausages were stored in a refrigerator for a few days and tested on taste.

Results

The sausages containing treated potassium lactate tasted better that sausages containing sodium lactate and sausages containing untreated potassium lactate. The aftertaste of the sausages containing treated potassium lactate was less than the aftertaste of sausages containing untreated potassium lactate. The potassium lactate-containing sausages were less salty than the sodium lactate-containing sausages. The sausages containing 3.3% treated potassium lactate tasted less salty than the sausages containing 2.5% sodium lactate.

The invention claimed is:

1. A process for the removal of undesirable flavours and odours from a potassium lactate solution, the method comprising:
   (a) heating the potassium lactate solution to a temperature between 20° C.-6020 C.; and
   (b) passing the potassium lactate solution continuously through a column of active carbon having a particle size of 0.5 to 3 mm,
   wherein undesirable flavours and odours are removed from the potassium lactate solution.

2. The process according to claim 1, wherein the active carbon is pre-treated by washing with hydrochloric acid and neutralising with sodium bicarbonate.

3. The process according to claim 1, wherein the potassium lactate solution comprises 40 to 80 % potassium lactate, based on the combined weight of water and potassium lactate.

4. The process according to claim 3, wherein the potassium lactate solution contains additional foodstuff additives.

5. The process according to claim 4, wherein the additional foodstuff additives are selected from acetic acid, sodium acetate, sodium diacetate, potassium acetate, potassium diacetate, citric acid, sodium citrate potassium citrate, or mixtures thereof.

6. The process according to claim 1, wherein the potassium lactate solution, after passage through the column of active carbon, is further supplied to a first filter whereby particles larger than 1 μm are removed.

7. The process according to claim 6, wherein after the first filter the potassium lactate solution is supplied to a second filter, whereby particles larger than 0.5 μm are removed.

8. The process according to claim 1, wherein the the potassium lactate solution has a residence time in the column of active carbon of 20 to 40 minutes.

9. The process according to claim 3, wherein the potassium lactate solution is mixed with active carbon, the solution is stirred during 20 to 40 minutes, and the active carbon is separated from the potassium lactate.

* * * * *

UNITED STATES PATENT AND TRADEMARK OFFICE
CERTIFICATE OF CORRECTION

PATENT NO. : 7,588,790 B2
APPLICATION NO. : 10/477134
DATED : September 15, 2009
INVENTOR(S) : Symone Kok et al.

It is certified that error appears in the above-identified patent and that said Letters Patent is hereby corrected as shown below:

At Column 4, line 30: --between 20°C.-6020 C.; and-- replace with: between 20° C - 60° C; and

Signed and Sealed this

Eighth Day of December, 2009

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,588,790 B2 |
| APPLICATION NO. | : 10/477134 |
| DATED | : September 15, 2009 |
| INVENTOR(S) | : Kok et al. |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 439 days.

Delete the phrase "by 439 days" and insert -- by 811 days --

Signed and Sealed this

Sixth Day of July, 2010

David J. Kappos
*Director of the United States Patent and Trademark Office*